(12) United States Patent
Taylor

(10) Patent No.: US 6,491,632 B1
(45) Date of Patent: Dec. 10, 2002

(54) METHOD AND APPARATUS FOR PHOTOGRAMMETRIC ORIENTATION OF ULTRASOUND IMAGES

(76) Inventor: Geoffrey L. Taylor, 120 Maryland Street, Winnipeg, Manitoba (CA), R3G 1L1

( * ) Notice: Subject to any disclaimer, the term of this patent is extended or adjusted under 35 U.S.C. 154(b) by 14 days.

(21) Appl. No.: 09/891,856

(22) Filed: Jun. 26, 2001

(51) Int. Cl.[7] .............................................. A61B 8/00
(52) U.S. Cl. ....................................... 600/443; 128/916
(58) Field of Search ................................. 600/407–471; 356/601, 613, 153; 345/441; 128/916, 922; 367/7, 11, 130, 138; 73/625, 626

(56) References Cited

U.S. PATENT DOCUMENTS

| | | | | | |
|---|---|---|---|---|---|
| 4,598,366 A | * | 7/1986 | Devaney | ...................... | 128/916 |
| 5,319,550 A | * | 6/1994 | Griffith | ........................ | 345/441 |
| 5,532,824 A | * | 7/1996 | Harvey et al. | .............. | 356/153 |
| 5,690,113 A | * | 11/1997 | Sliwa et al. | ................ | 128/916 |
| 5,776,062 A | * | 7/1998 | Nields | ........................ | 128/915 |
| 5,844,180 A | * | 12/1998 | Seale | ........................ | 310/90.5 |
| 5,876,342 A | * | 3/1999 | Chen et al. | ................. | 128/916 |
| 5,967,979 A | * | 10/1999 | Taylor et al. | ................ | 356/613 |
| 6,059,727 A | * | 5/2000 | Fowlkes et al. | ............ | 128/916 |
| 6,101,408 A | * | 8/2000 | Craine et al. | ............... | 128/922 |
| 6,306,091 B1 | * | 10/2001 | Sumanaweera et al. | ...... | 128/916 |
| 6,351,660 B1 | * | 2/2002 | Burke et al. | .................. | 359/32 |
| 6,381,026 B1 | * | 4/2002 | Schiff et al. | ................ | 356/601 |

* cited by examiner

Primary Examiner—Marvin M. Lateef
Assistant Examiner—Ali M. Imam
(74) Attorney, Agent, or Firm—William L. Chapin

(57) ABSTRACT

A method and apparatus for forming a three-dimensional image of a subsurface object utilizes an ultrasonic transducer wand to acquire ultrasonic images of an object, and a target plate attached to the wand which is optically imaged during each of a sequence of ultrasound scans, each of which is made with a different positioning of the ultrasonic scanning beam, thereby forming a sequence of quasi two-dimensional sonogram image slices of the object. Intersecting lines on the target are used to calculate a first coordinate transformation which transforms each optical image of the target plate and sensor to a normal view thereof, and each normally oriented target plate image is used to orient each sonogram image in a fixed coordinate system. A transformation matrix is then used to construct in a fixed coordinate system normalized two-dimensional sensor image slices of correct relative size, location, and orientation.

21 Claims, 12 Drawing Sheets

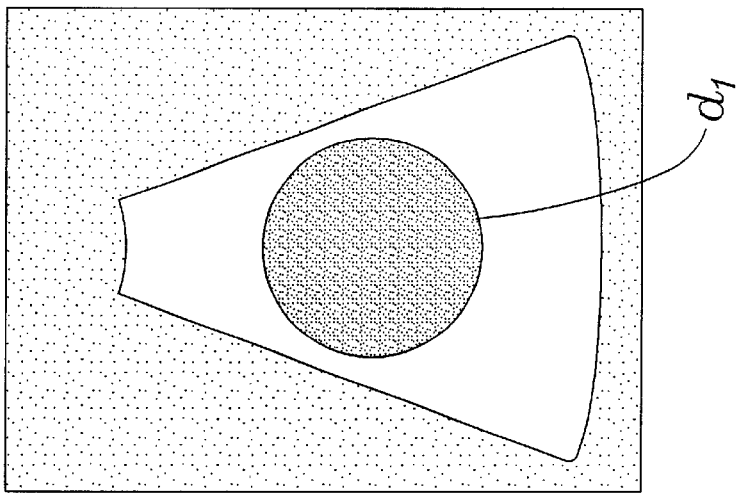
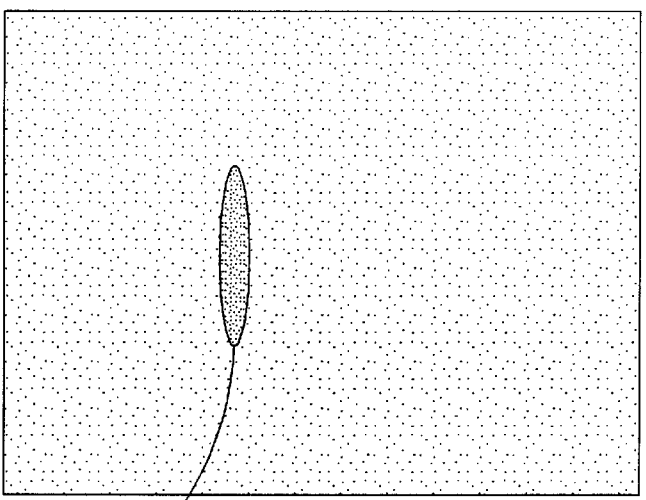
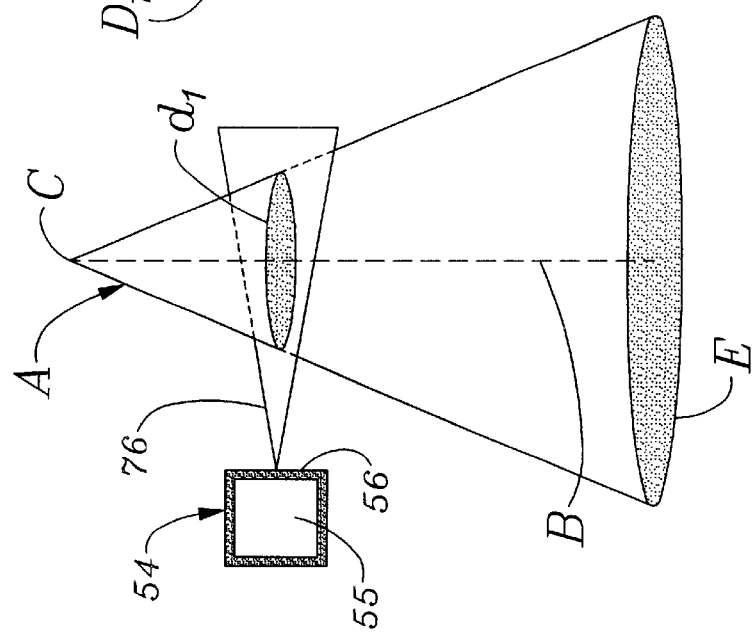

METHOD AND APPARATUS FOR PHOTOGRAMMETRIC ORIENTATION OF ULTRASOUND IMAGES

BACKGROUND OF THE INVENTION

A. Field of the Invention

The present invention relates to methods and apparatus for forming in a three-dimensional image space two-dimensional views of an object. More particularly, the invention relates to a method and apparatus for remotely measuring and recording the position and orientation of an ultrasonic imaging transducer while each of a plurality of two-dimensional image slices is obtained of an internal biological feature by the transducer, and assembling in a three-dimensional space accurately oriented scaled and proportioned views of the slices, thereby facilitating three-dimensional visualization of the feature.

B. Description of Background Art

Acquiring and viewing of two-dimensional ultrasound images has long been a useful non-invasive, non-destructive test method which yields valuable information enabling the visualization of otherwise invisible structures, in diverse fields such as medicine and materials inspection. For example, ultrasonic imaging is routinely used to acquire plan-view images of a fetus within the mother's womb, or of the otherwise invisible honeycomb cell structure in metal panels, so constructed to provide a high rigidity/strength-to-weight ratio. However, a problem exists with existing ultrasonic imaging techniques, particularly when these technologies are used to form images of irregularly shaped objects, including internal biological features (IBF's) such as a fetus. Thus, a three-dimensional visualization of an IBF oftentimes must be performed in real-time by a doctor or other healthcare professional who is acting as an ultrasonographer while a sequence of ultrasound scans are made on a patient. To form any ultrasonic image or sonogram of an IBF or other such feature, an ultrasonic imaging wand which contains an ultrasonic energy transducer is used. In a transmit mode, the transducer is electrically energized to transmit a fan-shaped scanning beam of ultrasonic energy; in a receive mode, the transducer receives ultrasonic signals reflected from an object and converts the ultrasonic signals to electrical signals which are used to form an image of the object on a monitor screen. The reflected signals received by the transducer are displayed on the screen in a two-dimensional pattern corresponding to the scanned beam of ultrasonic energy emitted by the transducer when the transducer is operated in the transmit mode, the brightness or color of displayed image elements or pixels on the screen being proportional to the strength of the received signals.

To form a three-dimensional visualization of an IBF or other feature of interest, a sequence of two-dimensional views or sonograms are made by varying the orientation and/or location of the ultrasound wand relative to the feature, thus causing the transmitted and received ultrasound beams to "slice" the feature at different angles and/or locations. Such "on-the-fly" visualizations of the three-dimensional shape of a feature, made from a sequence of two-dimensional image slices, is problematic for a number of reasons. For one thing, it requires a substantial degree of skill and experience to perform meaningful visualization. Moreover, the procedure requires that the wand be repositioned or panned continuously in the area of interest for time periods which may be discomforting to a patient. Also, there is no practical way to preserve on-the-fly mental visualizations of an IBF. Therefore, although it is possible to record and preserve individual sonograms, it is usually impractical if not impossible for the ultrasonographer to recreate three-dimensional views of results of an examination at a later date, or to transmit 3-D views to a different healthcare professional for his or her review.

There are existing machines which are capable of tracking the position and orientation of an ultrasonic imaging wand and associating the instantaneous position of the wand with the ultrasound image acquired at that time. However, such machines are extremely expensive and do not afford a capability for retrofitting to existing ultrasound machines.

In U.S. Pat. No. 5,967,979, issued Oct. 19, 1999, the present inventor, Geoffrey L. Taylor, disclosed with Grant D. Derksen a Method And Apparatus For Photogrammetric Assessment Of Biological Tissue. In that patent, a remote wound assessment method and apparatus was disclosed in which an oblique photographic image is made of a surface wound and a target object such as a plate containing a rectangular image and placed near the wound. Using a novel method of determining vanishing points where a photographic image of parallel lines on the target object intersect, coordinate transformations are calculated which map the oblique image of the rectangle into a normal image thereof. Using the same coordinate transformations, an oblique image of a wound adjacent to the target plate is mapped into a normal, i.e., perpendicular view thereof, allowing precise determination of the true size and outline shape of wound features. The '979 patent also disclosed an enhancement of the novel planar feature mapping method and apparatus with three-dimensional feature mapping. Thus, according to the method, two separate images of a wound and target plate are formed by moving the camera to two different locations which provide two different oblique views from which three-dimensional topographical features of a wound surface may be measured. Although the method and apparatus disclosed in the '979 patent have proved to be highly successful in evaluating surface features of biological tissue, the problem of conveniently forming three-dimensional views of internal biological features has been heretofore unsolved, motivating the present invention.

OBJECTS OF THE INVENTION

An object of the present invention is to provide a method and apparatus for forming from a plurality of two-dimensional image slices of an object a three-dimensional representation of the image slices.

Another object of the invention is to provide a method and apparatus for forming from a plurality of relatively thin image scans which intersect an object at different angles and/or from different vantage points a three-dimensional representation of the image slices, thus facilitating visualization of the object, including heights of various features of the object.

Another object of the invention is to provide a method and apparatus for forming from a plurality of thin image scans which intersect an object at different heights a three-dimensional representation of the image slices, thereby enabling visualization of the object including heights of various features of the object.

Another object of the invention is to provide a method and apparatus for remotely measuring in a three-dimensional coordinate space locations and orientations of a sensor used to gather data.

Another object of the invention is to provide a method and apparatus for remotely measuring the location and orientation of an ultrasonic transducer used to form ultrasound images whereby the location and orientation of features imaged by the transducer may be precisely reconstructed in a three-dimensional coordinate space.

Another object of the invention is to provide a method and apparatus which photogrammetrically monitors a target plate attached to an ultrasonic imaging transducer wand, as the wand is moved relative to an object of interest, and which performs coordinate transformations of a sequence of oblique images of the target plate to thereby map a sequence of relatively thin, quasi two-dimensional ultrasound image scans of an object obtained by the transducer wand at various orientations relative to the object into a sequence of object feature images of correct relative size, shape and location within a three-dimensional coordinate system, from which a three-dimensional visualization of the object is constructed.

Another object of the invention is to provide a method and apparatus for photogrammetrically monitoring ultrasonic image-forming scans of internal biological features, in which a target plate attached to a scanning ultrasonic transducer wand is photographically monitored to thereby determine and record the precise location and orientation of the wand during each of a sequence of scans, coordinate transformations of each oblique wand and target plate image performed to obtain a sequence of normal view images of the target plate, and, using the oblique-to-normal view transformations of target plate images, a sequence of ultrasonically formed scanned images or sonograms are assembled into a composite three-dimensional view from which internal biological features may be visualized.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, do not intend that the scope of my exclusive rights and privileges in the invention be limited to details of the embodiments described. I do intend that equivalents, adaptations and modifications of the invention reasonably inferable from the description contained herein be included within the scope of the invention as defined by the appended claims.

SUMMARY OF THE INVENTION

Briefly stated, the present invention comprehends a method and apparatus for photogrammetrically monitoring the position and orientation coordinates of a sensor being used to acquire a sequence of sensor images of an object, performing a first coordinate transformation to correctly orient the sensor images, and constructing a three-dimensional representation of the correctly oriented sensor images, thereby permitting three-dimensional visualization of the object.

According to the present invention, an optical imaging and recording instrument such as a video camera, camcorder or digital camera is used to form a sequence of photographic images, at arbitrary, typically oblique angles, of a target plate attached to an ultrasonic transducer wand while a sequence of ultrasound image scans is being made of an object of interest, e.g., a fetus within the mother's womb. During this step, a separate recorded image of the target plate and ultrasound wand is associated with each ultrasound image scan, which is typically a relatively thin, quasi two-dimensional "slice" of the object. A sequence of two-dimensional ultrasound image slices is formed by changing the orientation and/or location of the ultrasound wand for each scan, thus obtaining different ultrasound views of the object.

According to the present invention, the target plate has visual features of known dimensions which permit measurement of its distance from, and orientation with respect to a fixed monitoring device such as a video camera which may be temporarily secured to a fixed structure such as a bed on which a patient is lying. For example, the target plate may contain at least one pair of lines that intersect at a known angle, and preferably contains two pairs of parallel lines that are mutually perpendicular, forming a rectangle. When photographed at an arbitrary oblique angle, the image of the target rectangle is in general a quadrilateral. A coordinate transformation and image mapping method is then used to map the intersecting lines of an arbitrary image such as a quadrilateral into the rectangular "real world" shape of the target plate. A preferred method of performing the coordinate transformation and image mapping is that disclosed in U.S. Pat. No. 5,967,979. Using the same coordinate transformation which is used to map an oblique view of the image plate into a normal view thereof, the distance of the wand from the video camera, and its angular orientation with respect to the camera, may be precisely determined for each ultrasound image scan performed by the wand. Also, since the scan pattern of ultrasonic energy emitted by the wand bears a fixed relationship to the wand, precisely determining the position and orientation of the wand precisely determines the location and orientation of each ultrasound image slice relative to a patient and object of interest. The novel method and apparatus according to the present invention utilizes that information to calculate a coordinate transformation matrix which is then used to construct a three-dimensional image representation of the sequence of two-dimensional image slices, utilizing the orientation and position of each slice relative to a fixed reference frame. This three-dimensional image representation of sensor image slices enables an object scanned by the sensor to be visualized in three dimensions.

BRIEF DESCRIPTION OF THE DRAWINGS

FIG. 4 is a diagrammatic perspective view showing the orientation of a target plate affixed to an ultrasound imaging wand, the beam pattern of imaging energy emitted by the wand, and an idealized object scanned by the beam at a first position and orientation to form a first sonogram consisting of a first two-dimensional image slice of the object.

FIG. 5 is a plan view of the first sonogram obtained as shown in FIG. 4.

FIG. 6 is a perspective view in which the first sonogram comprising a two-dimensional object image slice obtained as shown in FIG. 4, has been properly oriented, shaped and sized with respect to a fixed reference frame by the same coordinate transformation used to form a normal view of the target plate.

DESCRIPTION OF THE PREFERRED EMBODIMENTS

FIGS. 1–22 illustrate an apparatus and methods according to the present invention for photogrammetrically orienting two-dimensional ultrasound image slices of an object into a three-dimensional view of the image slices, thereby enabling three-dimensional visualization of the object.

Figure 1:
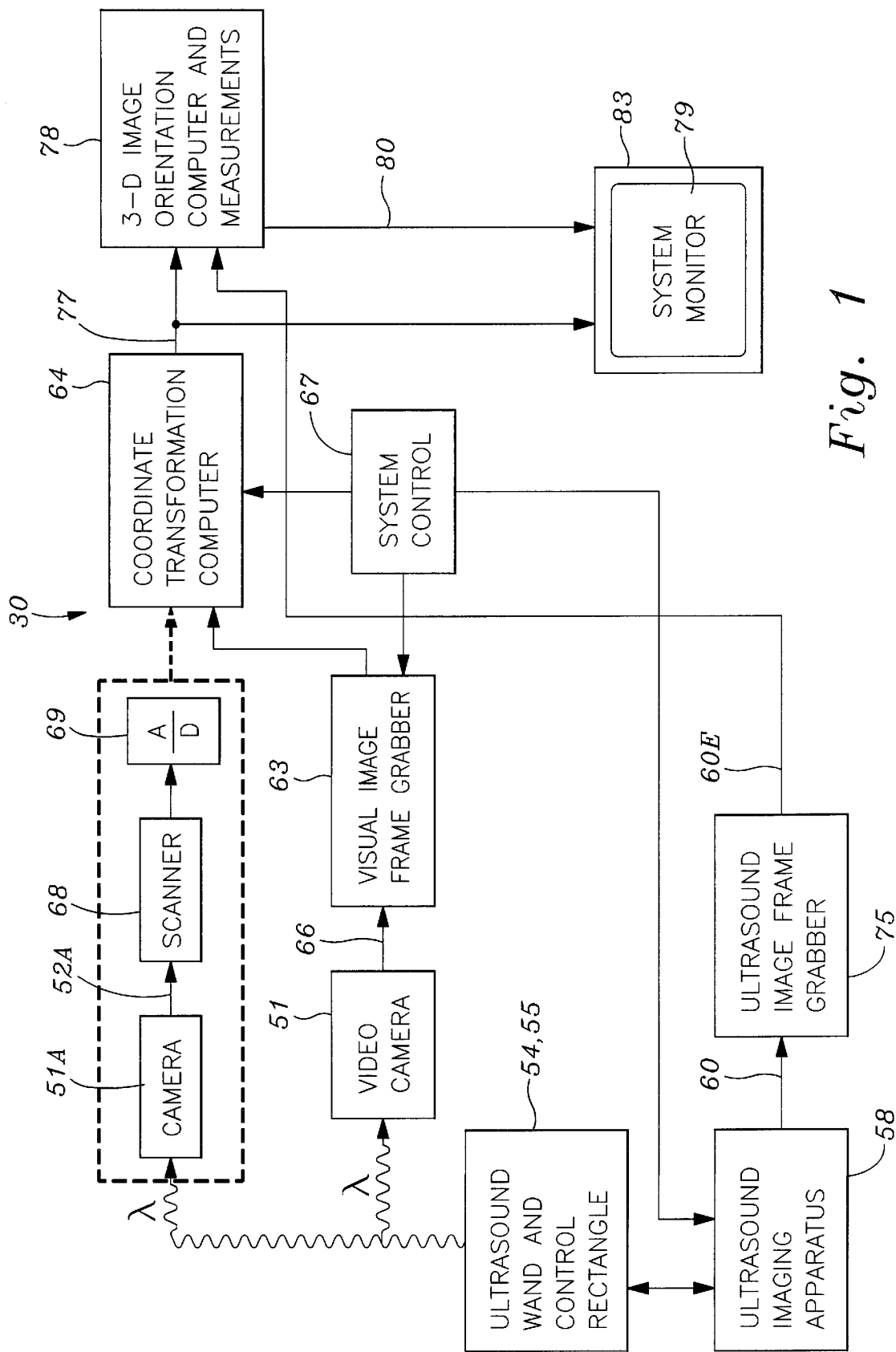
FIG. 1 is a block diagram of an apparatus for photogrammetric orientation of ultrasound images according to the present invention.
Figure 2:
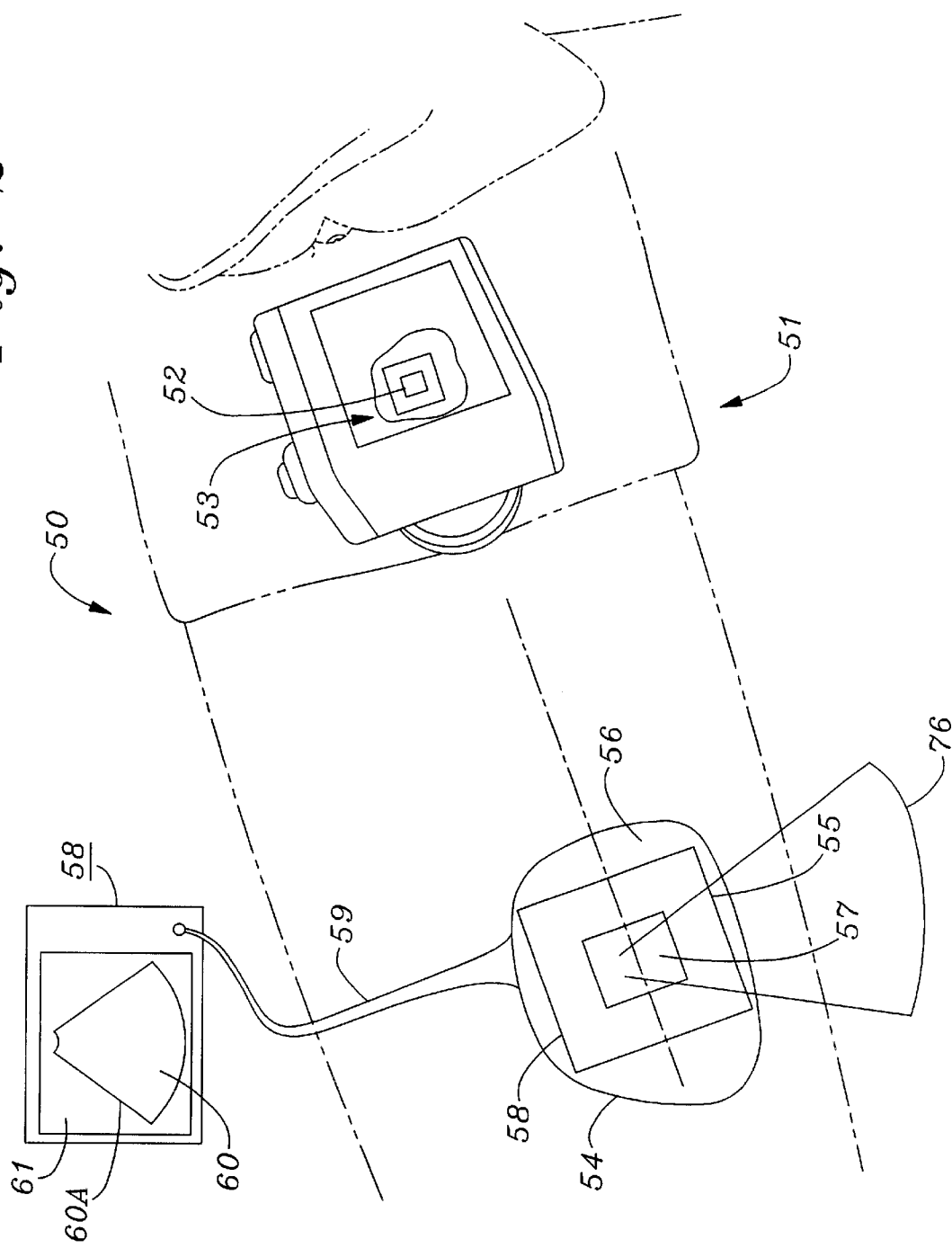
FIG. 2 is a partially diagrammatic perspective view of an image acquisition portion of an apparatus for photogrammetric orientation of ultrasound images according to the present invention.
Figure 3:
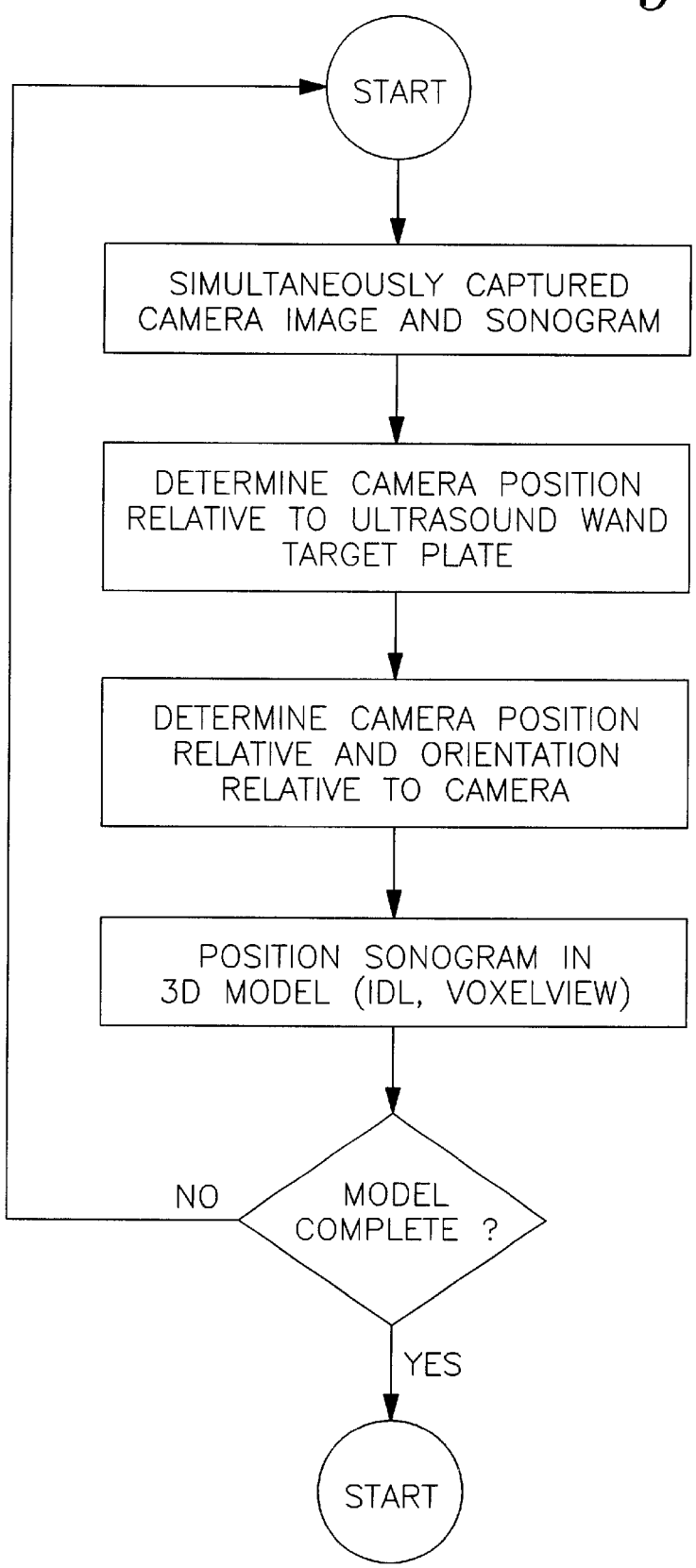
FIG. 3 is a simplified flow chart showing operation of the present invention.

Referring first to FIGS. 1 and 2, an apparatus 30 for photogrammetric orientation of ultrasound images according to the present invention may be seen to include an image acquisition apparatus 50. As shown in FIG. 2, image acquisition apparatus 50 according to the present invention includes a visual imaging device 51 which is capable of recording a sequence of optical images. Thus, imaging device 51 may be a still photographic film camera such as a 35 mm camera or film motion picture camera. Preferably, however, imaging device 51 is of a type which produces real-time electronic representations of an optical image, rather than one such as a film camera which requires photographic processing of film and subsequent electro optical scanning of film images to obtain electronic images. Thus, imaging device 51 is preferably a digital camera or camcorder. Alternatively, imaging device 51 may consist of a video camera that outputs an electronic image signal which is recorded on an external electronic memory such as a computer hard disk, floppy disk, or the like.

Referring still to FIG. 2, it maybe seen that imaging device 51 is used to form an image 52 at the focal plane 53 of the device. As shown in FIG. 2, imaging device 51 is fixed with respect to a stationary object, such as a hospital bed (not shown), and has a field of view which encompasses an ultrasonic imaging transducer wand 54 located in proximity to a subject such as a patient lying on a hospital bed. Wand 54 has affixed thereto a target plate 55 which has contrasting visual features of a predetermined size and shape. In the example embodiment of image acquisition apparatus 50 shown in FIG. 2, ultrasonic imaging transducer wand 54 has a bulbous shape similar to that of an egg cleaved along a vertically disposed medial plane parallel to the long axis of the egg to form a flat front surface 56. This type of transducer emits an ultrasonic energy beam which is directed in a generally conically shaped scan pattern having a triangular trace in a plane generally perpendicular to front surface 56 of the transducer, and produces a similarly shaped ultrasound image field pattern, as shown in FIGS. 4 and 5.

Referring still to FIG. 2, it may be seen that target plate 55, which is preferably mounted flush with and parallel to front face 56 of ultrasonic transducer wand 54, has a generally rectangular, preferably square shape, and has a rectangular central area 57 concentric with the perimeter 58 of the target plate. Central area 57 of target plate 56 is preferably of a different color or darkness than the remainder of the target plate. Thus, as shown in FIG. 2, central area 57 of target plate 55 may be of a light color, such as while, while the remainder of the target plate may be of a darker color, such as black.

Referring still to FIG. 2, it may be seen that apparatus 30 includes an ultrasonic imaging apparatus 58 which is connected by an electrical cable 59 to ultrasonic imaging transducer wand 54. Ultrasonic imaging apparatus 58 is of a conventional type, such as a General Electric brand LOGI Q 500 model number. The construction and function of typical ultrasonic imaging apparatus of this type is described in Havlice and Taenzer, "Medical Ultrasonic Imaging: An Overview of Principles and Instrumentation," *Proc. IEEE.* Vol. 67. pp. 6200–641. April 1979.

Ultrasonic imaging apparatus 58 contains electronic circuitry for producing electrical signals of ultrasonic frequency which drive a piezoelectric or magnetostrictive ultrasonic transducer in wand 54, and cause the transducer to emit a beam of energy directed to an object of interest, such as a fetus or other Internal Biological Feature (IBF). Typically, the ultrasonic energy beam emitted by the transducer in wand 54 is mechanically or electronically scanned to form a generally fan-shaped pattern, i.e., in the shape of a truncated isosceles triangle with the vertex located at the transducer, as shown in FIGS. 2, 4 and 5. This type of scan format is referred to as a sector scan. During a period when ultrasonic drive energy to the transducer within transducer wand 54, is interrupted, the transducer functions in a receive mode, converting ultrasound signals reflected from an IBF into electrical information signals. The latter are used to form an image 60 of a region scanned, the image being displayed on the screen of a LCD, CRT or other display device monitor 61.

Image 60 appears on monitor 61 within an active display area 60A shaped similarly to the scan pattern of the ultrasonic energy beam transmitted by transducer wand 54. In this display, referred to as a B-scan or brightness mode scan, the angular coordinate position of an object feature in the scanned image field 60A is indicated by the angular position of radial display lines corresponding to the instantaneous directions of an ultrasonic energy beam emitted by the transducer. Radial coordinate positions of an object from the common vertex of ultrasound energy beam scan lines, which intersect at the transducer, are determined by measuring the time delay between the emission of an ultrasonic energy pulse, and a return signal reflected from a feature and received by the transducer. The radial coordinates of object features in display area 60A of monitor 61 are displayed at a proportional distance from the vertex of the display area, and the strength of the reflected signals are indicated by modulating the brightness of display pixels. Ultrasound imaging apparatus 58 also includes electronic memory means 62 for storing a sequence of ultrasound images 60, referred to as sonograms.

Referring now to FIG. 1, it may be seen that apparatus 30 according to the present invention includes components functionally interconnected with visual image acquisition apparatus 50 and ultrasonic imaging apparatus 58 shown in FIG. 2 and described above, to perform a photogrammetric orientation of ultrasound images according to the method of the present invention.

As shown in FIG. 1, apparatus 30 includes a computer 64. As will be described in greater detail below, computer 64 is utilized to precisely determine the instantaneous location and orientation of :ultrasonic imaging wand 54 relative to a fixed imaging device 51 for each two-dimensional image slice or sonogram in a sequence of sonograms obtained by changing the orientation and/or location of the wand relative to an Internal Biological Feature (IBF) or other feature of interest. This step is performed by forming an oblique view image of target plate 55 with imaging device 51, and transforming and scaling the oblique image into a correctly scaled normal view image of the target plate using the method described in detail in U.S. Pat. No. 5,967,979, the entire disclosure of which is hereby incorporated by reference into the present specification.

Since target plate 55 is fixed to ultrasound scanning wand 54, precisely determining the orientation and location of target plate 55 precisely determines the orientation and location of the ultrasound scanning wand. Therefore, the method described in the '979 patent enables determination of the precise orientation of the scanned ultrasound energy beam relative to a feature of interest, and therefore the location and orientation of sonogram slices obtained of the feature. According to the present invention, the precise orientation and location of each sonogram slice relative to a fixed coordinate reference frame, e.g., one in which a patient and imaging device 51 are fixed, is used to construct an assembly of correctly scaled and oriented three-dimensional views of ultrasound image slices of the object, using software such as VOXELVIEW, version 1.0, obtainable from Vital Images, Inc., 3300 Penbrook Avenue North, Plymouth, Minn. 55447, or IDL, version 3, also obtainable direction from Vital Images. This enables the object to be visualized in three dimensions.

Referring still to FIG. 1, it may be seen that apparatus 30 according to the present invention includes means for inputting into computer 64 electronic image signals of wand 54 and target plate 55 obtained by imaging device 51, the computer being used to compute instantaneous normal view images of the target plate and wand. Apparatus 30 also includes means for inputting into computer 64 a sequence of electronic image frames, one for each sonogram that represents a two-dimensional image slice of an internal biological features.

As shown in FIG. 1, apparatus 30 includes a first, visual image frame grabber 65 which converts each visual image signal 66 obtained by optical imaging device 51 into a separate frame of image data for each of a sequence of images. Operation of visual image frame grabber 65 is controlled by a system control electronic module 67, which issues a command signal, timing signal, and frame identification signal when it is desired to capture and store a particular image frame input to the frame grabber by optical imaging device 51. Each optical image frame thus captured and stored is electronically identified with a sonogram obtained simultaneously with the optical image of transducer wand 54 and target plate 55, thus recording the precise orientation and location of the wand during the sonogram scan. Frame capture command signals may be issued at predetermined times by system control module 67, or manually by an external command instruction issued by the ultrasonographer. Although system control module 67 is shown in FIG. 1 to be separate from computer 64, functions of the system control module could of course be performed by the computer with appropriate interface electronics and software, as will be understood by those skilled in the art.

As shown in dashed lines in FIG. 1, imaging device 51 could optionally be replaced by a photographic still camera 51A. In this case, a separate photographic film image 52A is made of ultrasonic wand 54 and target plate 55 for each sonogram obtained using the wand. The exposed film must then be processed in a conventional manner to develop the latent photographic images on the film, the developed film images scanned using an optical scanner 68 and an analog-to-digital (A/D) converter 69 used to convert the analog two-dimensional film image into a digital image, which is input into computer 64 in place of electronic images output from frame grabber 65. However, because of the difficulty of synchronizing real-time sonograms with subsequently processed photographic film image, electronic imaging by video camera 51 is a preferred method. Alternatively, camera 51A could be a digital camera, in which case scanner 68 and A/D converter 69 would be replaced by a digital memory means such as a flash memory card.

Referring still to FIG. 1, it may be seen that apparatus 30 includes a second, ultrasound image from grabber 75 which converts electronic ultrasound image, signals 60E corresponding to sonograms 60 obtained by ultrasonic imaging apparatus 58 into a separate frame of image data for each of a sequence of sonograms showing separate image slices of an internal biological feature. Each ultrasound image frame 60E corresponding to a separate sonogram 60 is stored electronically along with a timing code and identification code that associates each sonogram with an optical image frame of the transducer wand 54 and target plate obtained simultaneously with the particular sonogram.

As described above computer 64 of apparatus 30 performs on each optical image 66 of wand 54 and target plate 55 a coordinate transformation which determines the precise orientation and location of the wand at the time a sonogram 60 associated with the optical image is formed. Since the ultrasonic fan beam emitted by transducer wand 54 to form a sonogram image bears a fixed geometric relationship to the transducer, determining the precise location and orientation of the wand determines the exact trajectory of the image-forming beam relative to a fixed reference frame. In a typical example embodiment of the present invention, an ultrasound beam 76! is emitted in a plane perpendicular to front face 56 of the transducer wand, with the vertex of the beam located behind the front face and centered on a longitudinally disposed, vertical medial plane of the wand, as shown in FIG. 2.

Construction of a three-dimensional assembly of two-dimensional sonograms taken at different orientations of ultrasound beam 76 is performed by apparatus 30 in the following manner.

Referring again to FIG. 1, it may be seen that transformed normal view images 77 of ultrasound wand 54 and target plate 55 are input to a computer 78, which may be part of computer 64. The transformed normal view images are used to indicate the relative spacing between ultrasound wand 54 and an object of interest, and the orientation of the wand relative to the object, for each sonogram obtained of the object. Using this information, computer 78 constructs in a three-dimensional image space 79 three-dimensional images of a sequence of two-dimensional sonogram image slices, in the manner shown in the following example.

Referring now to FIG. 4, a solid cone A is shown as an example object of interest to be visualized using the method and apparatus 30 according to the present invention. As shown in the example of FIG. 4, cone A, which could as well be a fetus or other internal biological feature of interest to an ultrasonographer, is scanned by a beam 76 emitted by ultrasound wand 54 having a first location and orientation to form a first sonogram. The position and orientation of the want relative to cone A during the first scan are determined by calculating the size and orientation of visual features on target plate 55, using the coordinate transformation described in U.S. Pat. No. 5,967,979 and cited above. As shown in FIG. 4, the orientation of front face 56 of transducer wand 54 is parallel to the central, vertically orientated axis B of cone A. With this arrangement, ultrasound image beam 76 lies in a horizontal plane which intersects cone A a short distance below the vertex C of the cone. Thus, a first sonogram of cone A, as shown in FIG. 5, consists essentially of a circular area having a first diameter, $d_1$. Using the VOXELVIEW reconstruction software described above, a first image slice is therefore reconstructed which is a circle of a first diameter, $D_1$, scaled in a ratio K to $d_1$, and in a three-dimensional image space 79, shown in FIG. 6, a perspective view of circle $D_1$, is constructed.

Figure 7:
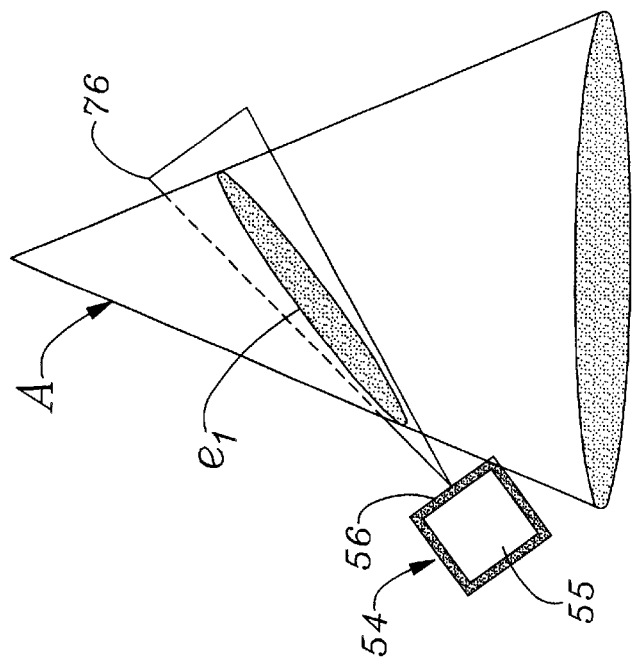
FIG. 7 is a view similar to that of FIG. 4, but showing the wand and target plate of FIG. 4 oriented to obtain a second two-dimensional image slice of the object.
Figure 9:
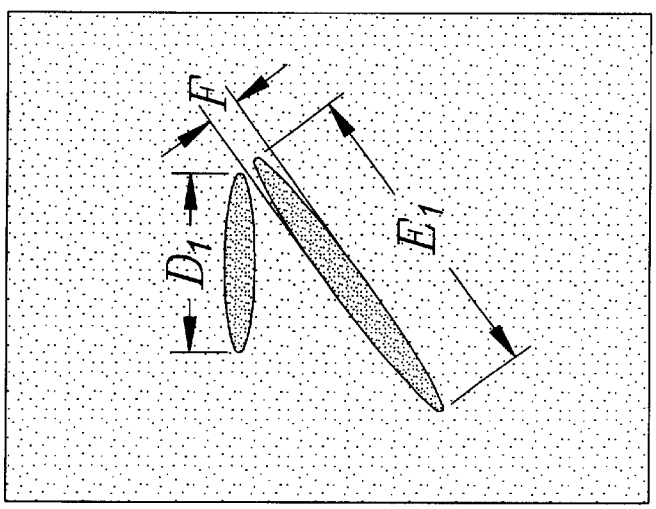
FIG. 9 is a view similar to that of FIG. 6, but showing a transformed image of the second two-dimensional image slice added thereto.
Figure 8:
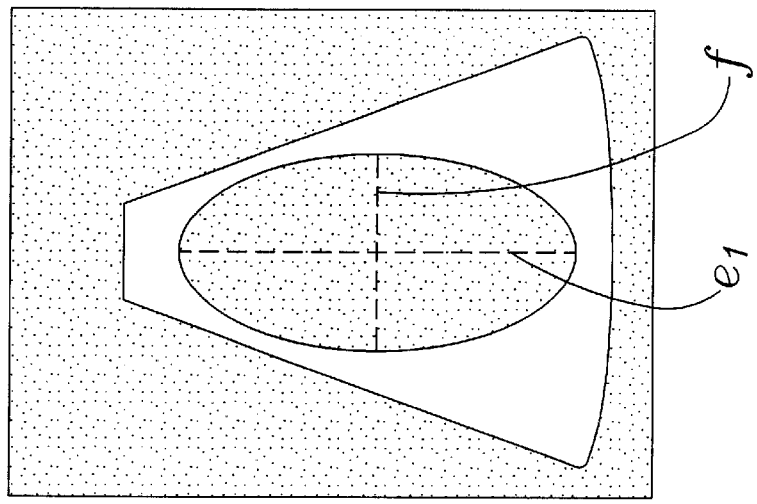
FIG. 8 is a plan view of the second sonogram obtained as shown in FIG. 7.

Next, as shown in FIG. 7 of the present example, ultrasonic imaging wand 54 is relocated to a second position, e.g., a position lower than that shown in FIG. 4, and the wand tilted obliquely upwards with respect to its orientation shown in FIG. 4. At this second location and orientation, a second sonogram is made of cone A, with fan beam 76 of wand 54 intersecting the cone at an oblique angle. Thus, as shown in FIG. 8, a second sonogram of cone A consists essentially of an elliptically shaped area having a major axis e, and a minor axis f. Using the VOXELVIEW reconstruction software, a reconstruction of the second sonogram image slice in three-dimensional image space 79, as shown in FIG. 9, is therefore an ellipse having a major axis E, and a minor axis F that are scaled in the same ratio K used to scale each sonogram into three-dimensional image space 79.

Figure 11:
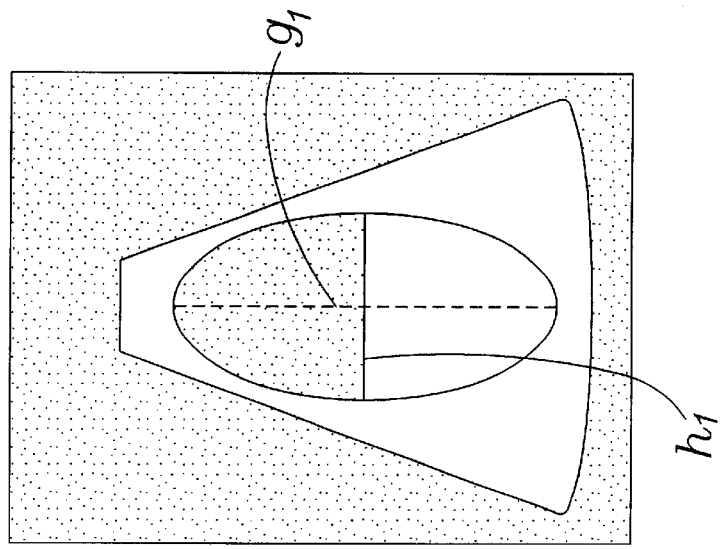
FIG. 11 is a plan view of the third sonogram obtained as shown in FIG. 10.
Figure 12:
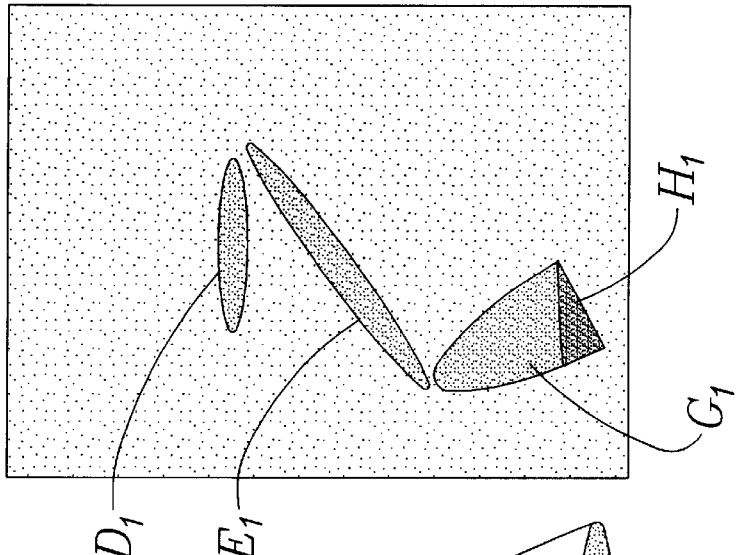
FIG. 12 is a view similar to that of FIG. 6, but showing a transformed image of the third two-dimensional image slice added thereto.
Figure 10:
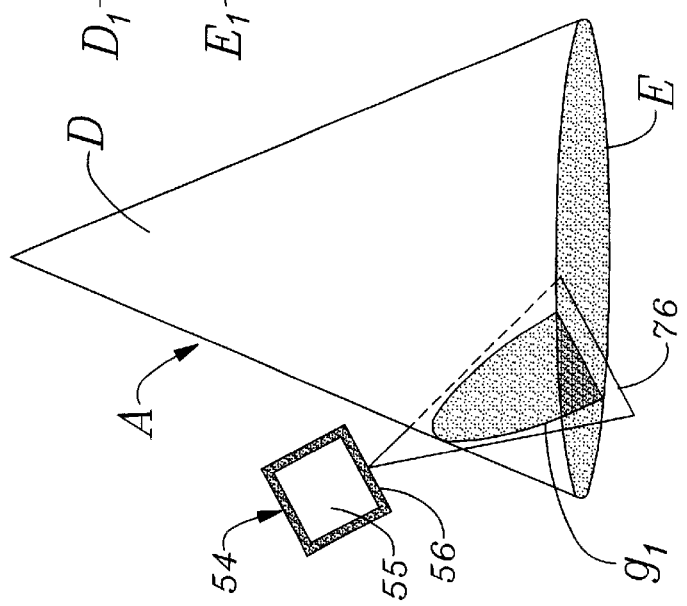
FIG. 10 is a view similar to that of FIG. 4, but showing the wand and target plate of FIG. 4 oriented to obtain a third two-dimensional image slice of the object.

FIG. 10 of the present example shows ultrasonic imaging want 54 oriented to a third position intermediate in height between positions 1 and 2 shown in FIGS. 4 and 7, but inclined obliquely downward from a horizontal plane. At this third location, a third sonogram is made of cone A, with fan beam 76 of wand 54 intersecting the surface D and base E of the cone at an oblique angle. Thus, as shown in FIG. 11, a third sonogram of cone A consists essentially of a semi-elliptical area having a major axis g, and a truncating chord h. Using the VOXELVIEW reconstruction software, a reconstruction of the third sonogram slice in three-dimensional image space 79 as shown in FIG. 12, is therefore a semi-ellipse having a major axis G, and a truncating chord H, that are scaled in the ratio K used to scale each sonogram into three-dimensional space 79.

Figure 13A:
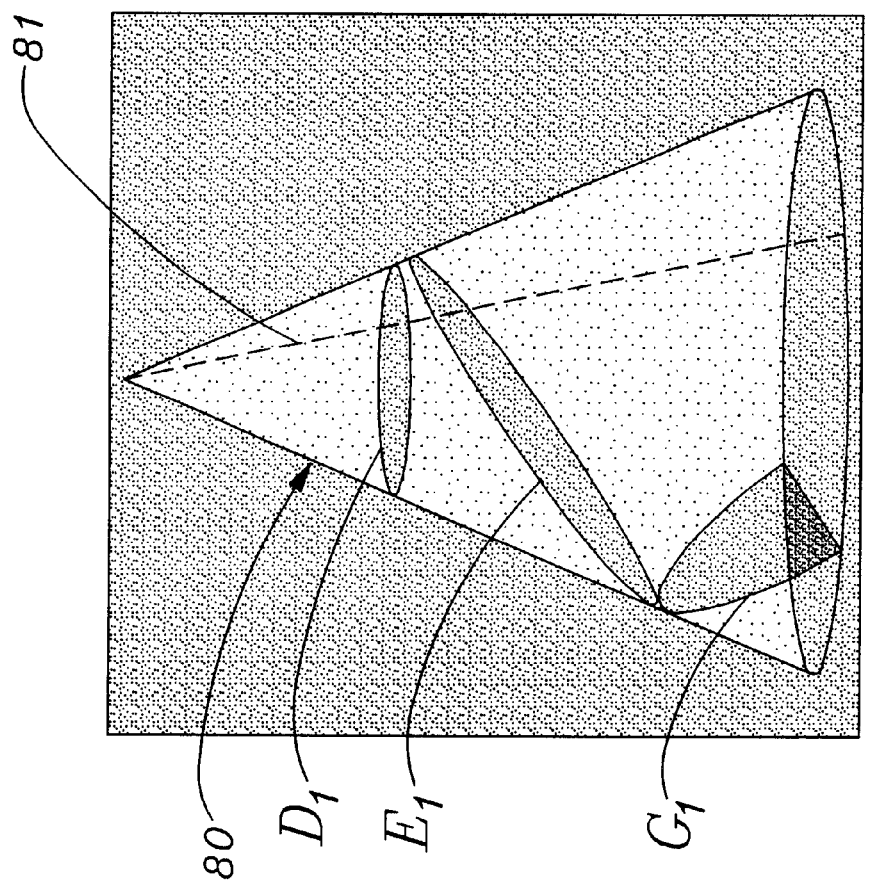
FIG. 13A is a perspective view showing a partial image of the object of FIG. 4, in which the partial image is properly oriented, shaped and sized relative to a fixed reference frame.
Figure 13B:
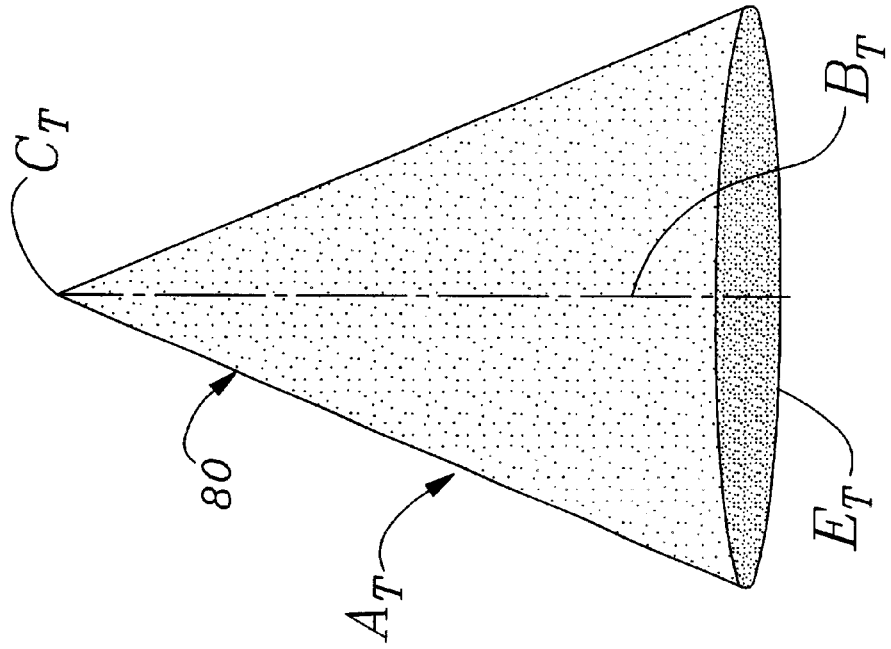
FIG. 13B is a perspective view showing a complete image of the object of FIG. 4, in which the image is properly oriented, shaped and sized relative to a fixed reference frame.

FIG. 13A shows a three-dimensional image space 79 in which the transforms of sonogram images shown in the example FIGS. 4–12 have been assembled together in a properly arranged and scaled and oriented relationship. FIG. 13B shows a surface 80 which is constructed using the rendering portion of the VOXELVIEW program, visually, for example, by mentally extending a plurality of directrix lines 81 through the perimeters of a stack of substantially planar image transforms. As shown in FIG. 13B, surface 80 formed by directrix lines 81 defines a conical transferred image object A, having an altitude $B_1$ and a base $E_1$ which is a correctly scaled and proportioned representation of the object cone scanned by ultrasound fan beam 76.

Figure 14:
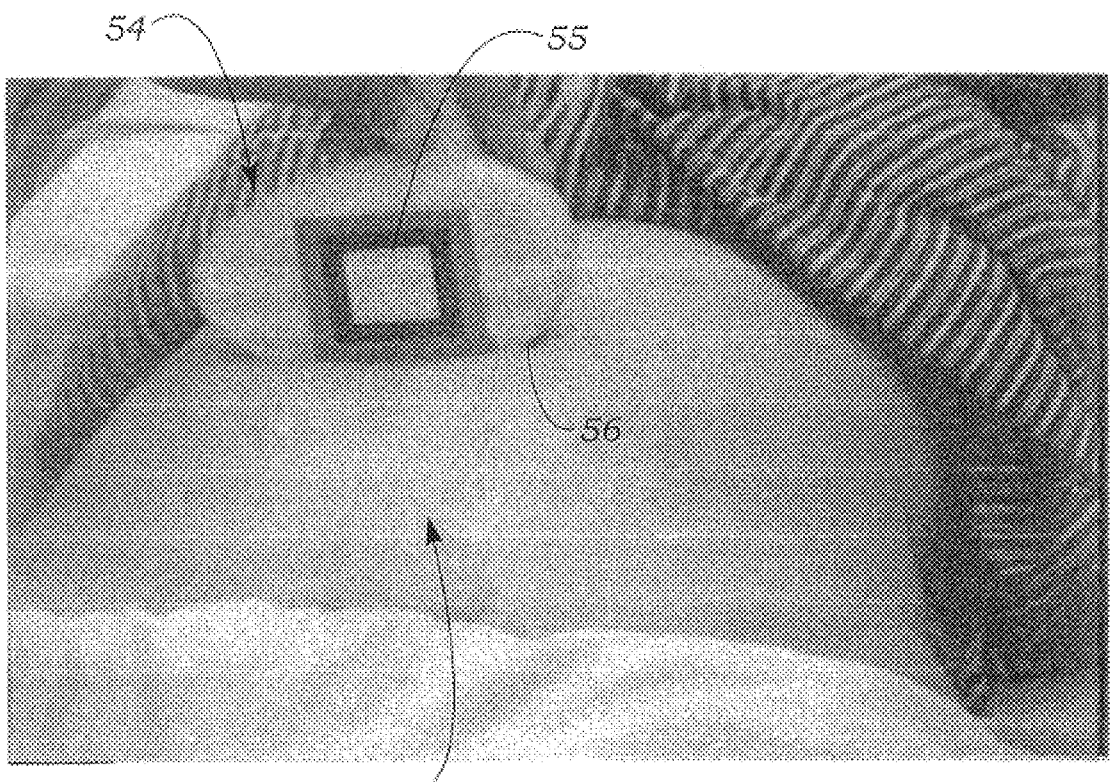
FIG. 14 is a perspective view showing an ultrasonic imaging transducer wand and target plate according to the present invention, located in a first position and orientation on the abdomen of a patient.
Figure 15:
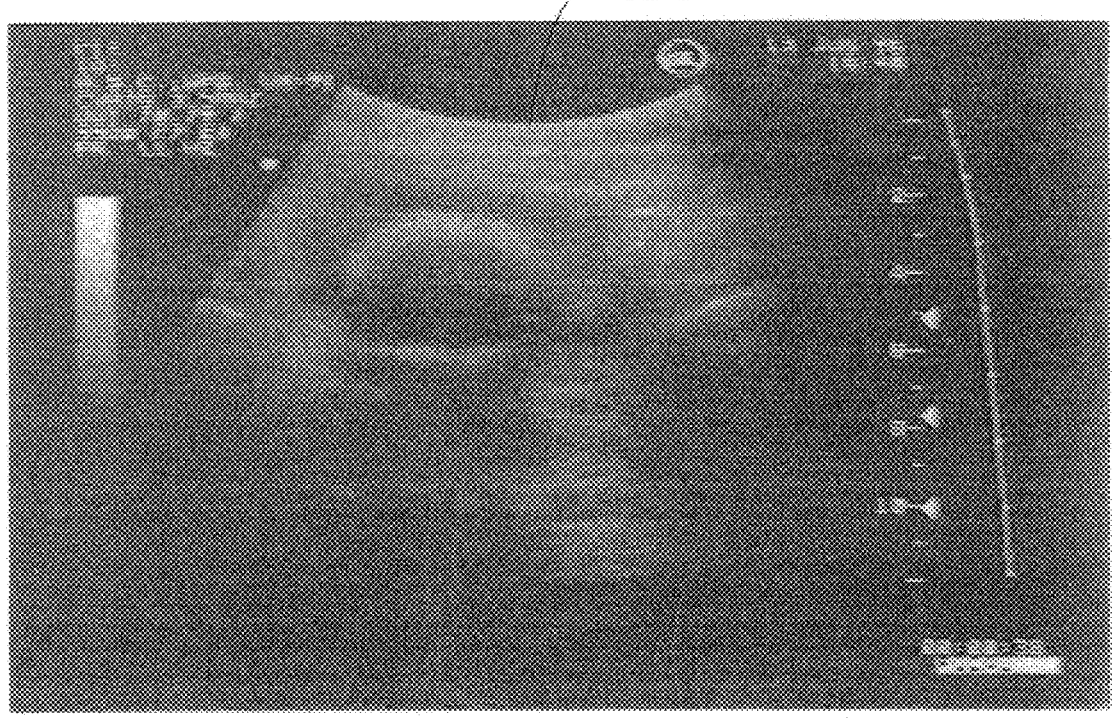
FIG. 15 is a photographic view of a CRT screen showing an ultrasound image slice obtained with the arrangement shown in FIG. 14.

Referring now to FIGS. 14–21 it may be seen how apparatus 30 according to the present invention is used to form a three-dimensional visualization of an actual object of interest using the method shown in FIGS. 4–13 and described above. Thus, as shown in FIG. 14, ultrasonic imaging wand 54 is located in a first position and at a first orientation relative to the abdomen J of a patient K. At this first position and orientation of transducer wand 54, a first sonogram 82-1, shown in FIG. 15, is obtained of an internal biological feature (IBF) such as a fetus L.

Figure 16:
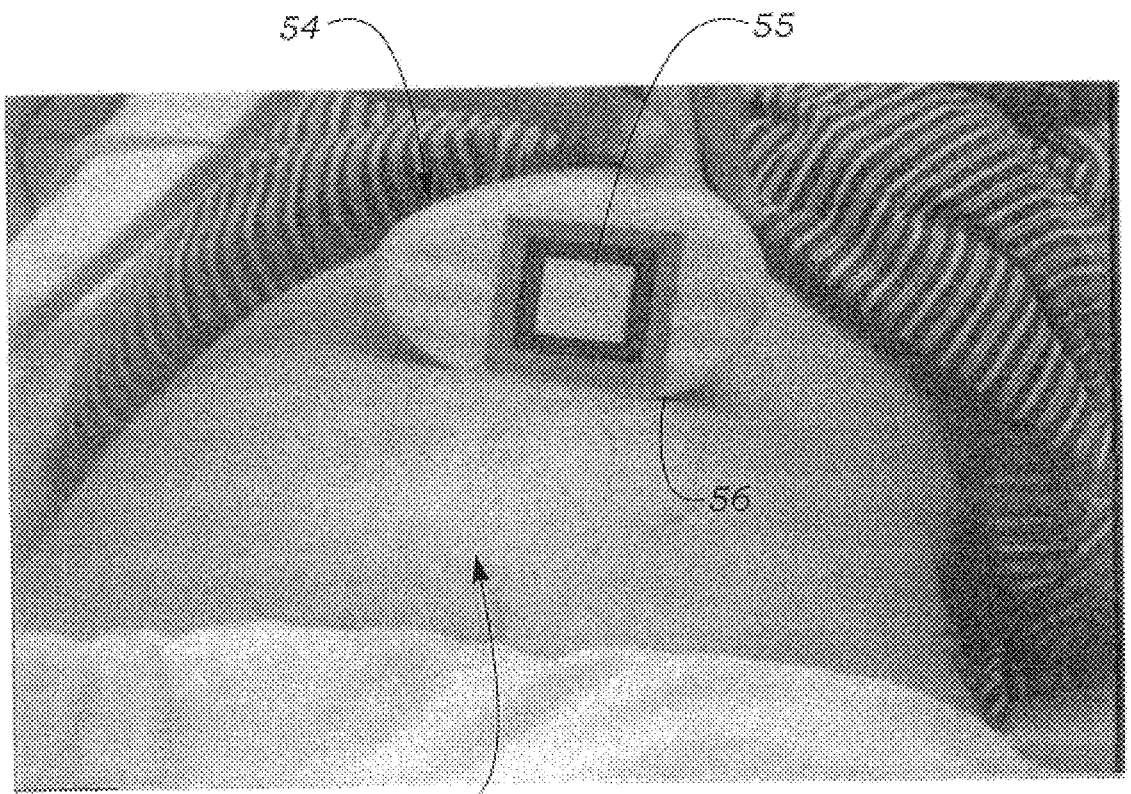
FIG. 16 is a view similar to that of FIG. 14, but showing the wand at a second position and orientation.
Figure 17:
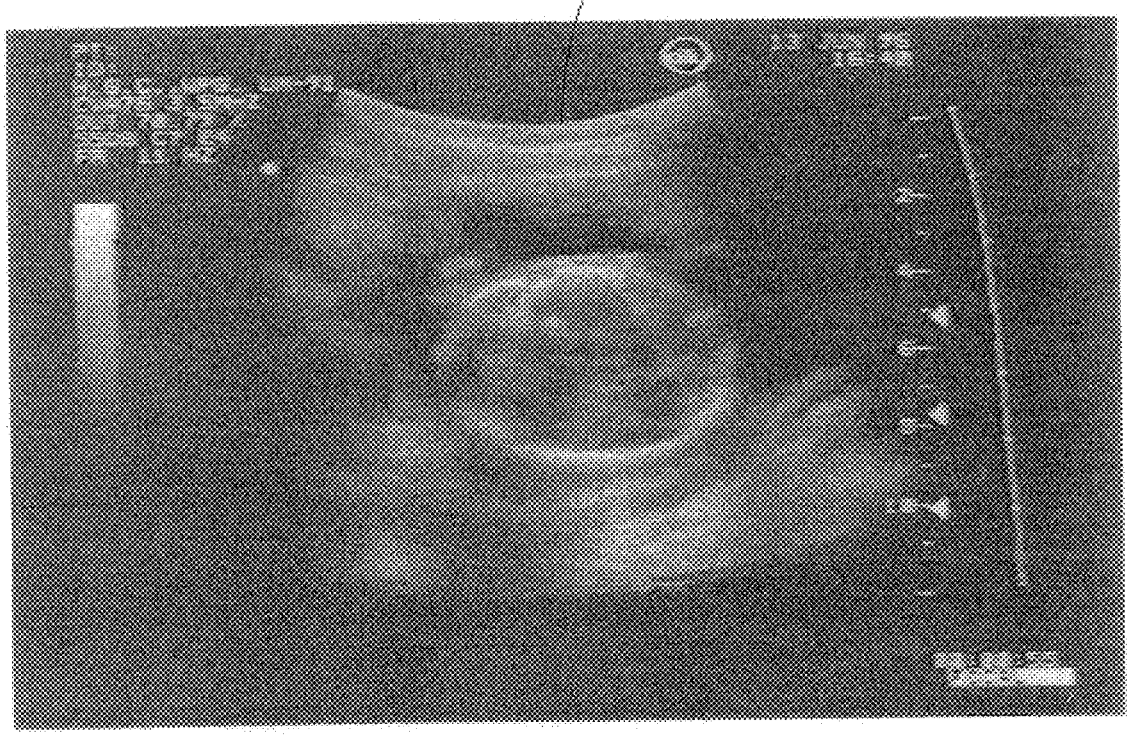
FIG. 17 is a view similar to that of FIG. 15, but showing a CRT display for the ultrasound image slice obtained with the ultrasound wand located as shown in FIG. 16.
Figure 18:
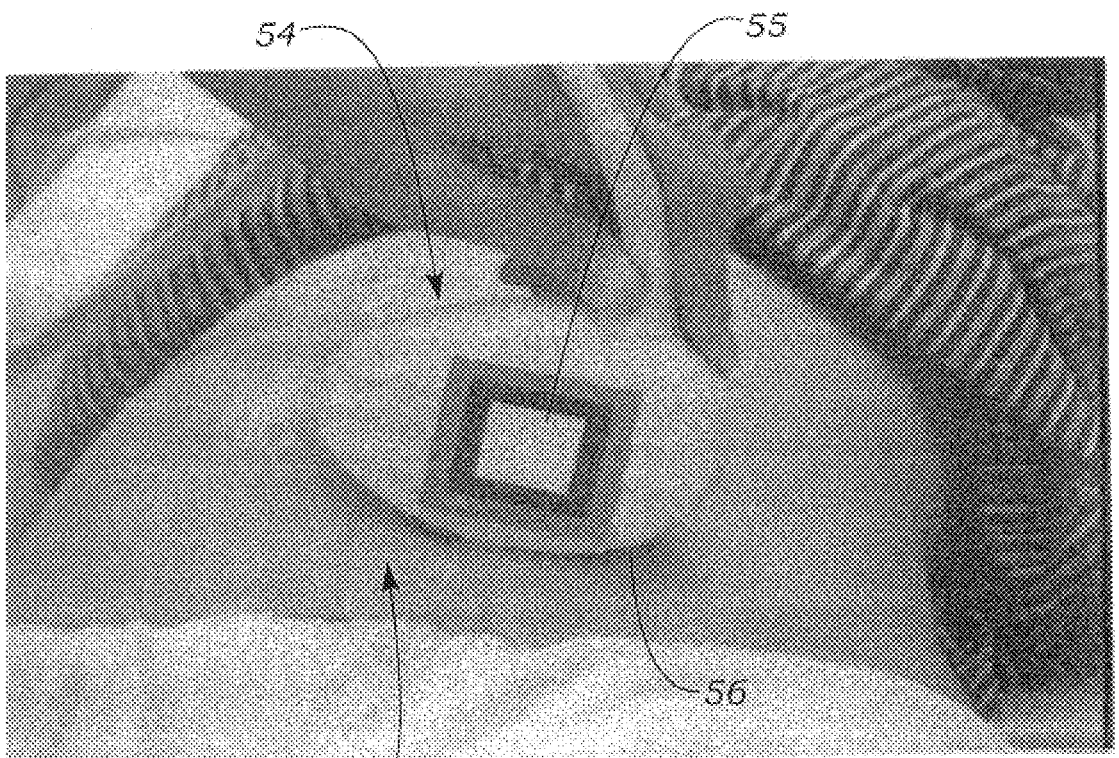
FIG. 18 is a view similar to that of FIG. 14, but showing the wand at a third position and orientation.
Figure 19:
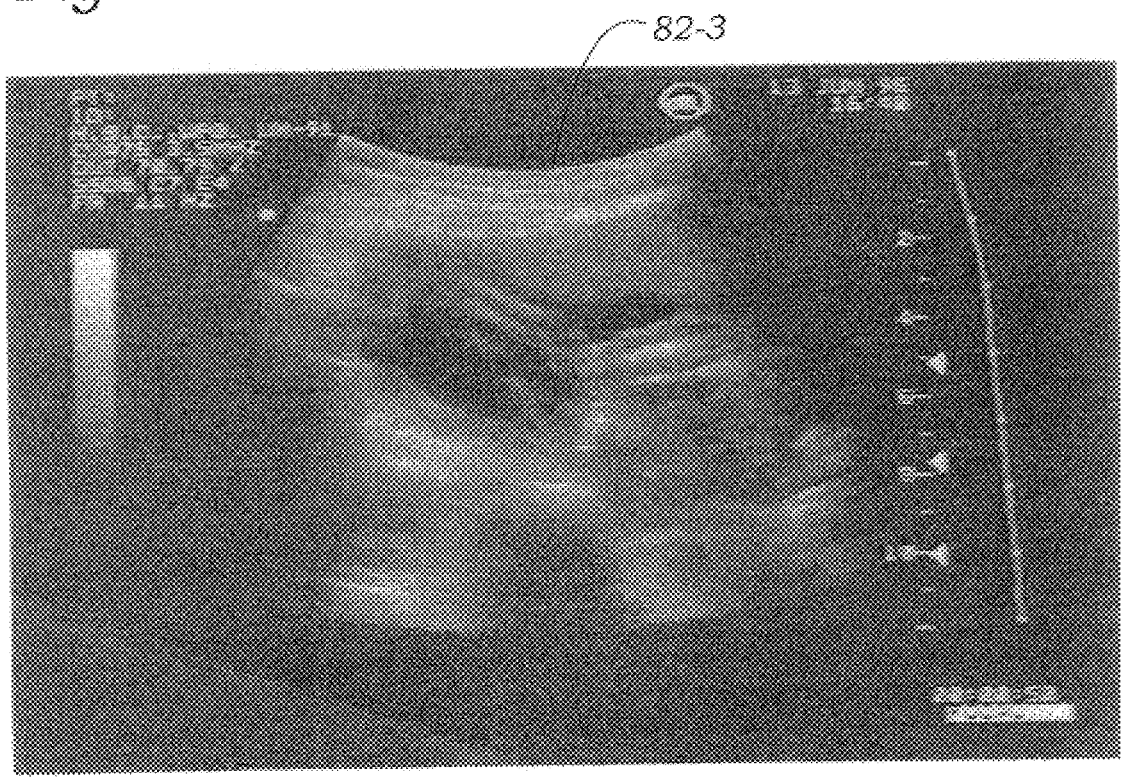
FIG. 19 is a view similar to that of FIG. 15, but showing the CRT display for an ultrasound image slice obtained with the ultrasound wand located as shown in FIG. 18.
Figure 20:
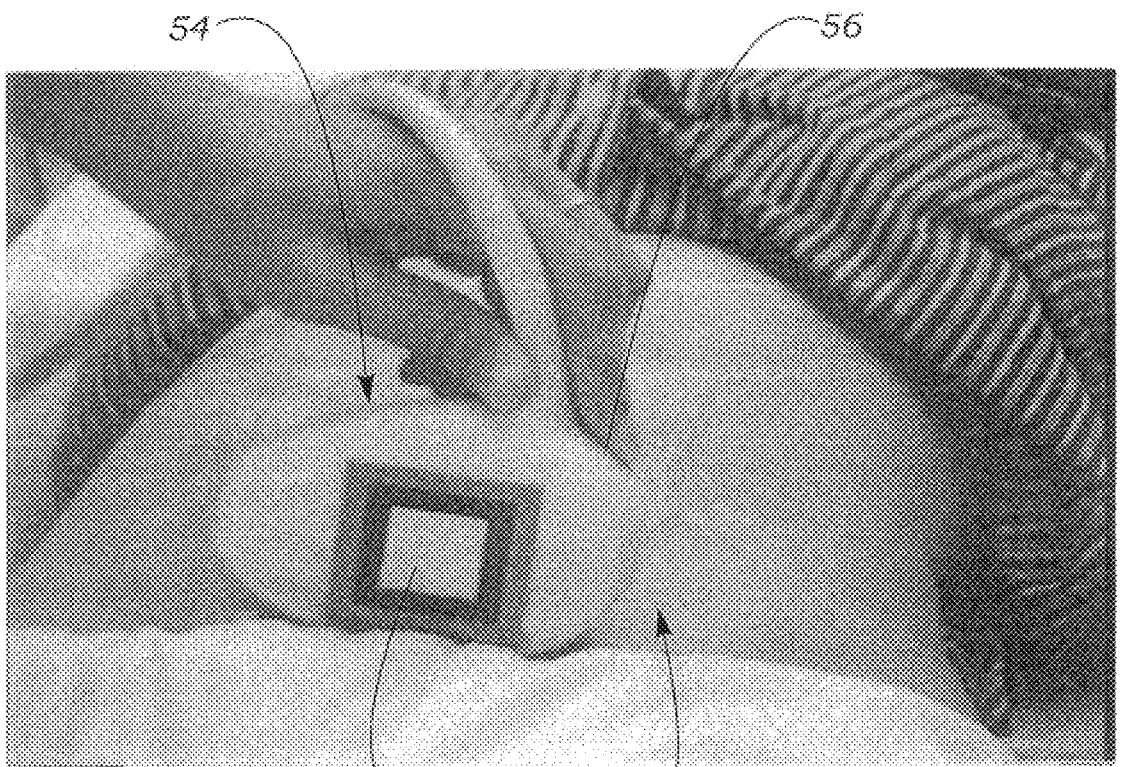
FIG. 20 is a view similar to that of FIG. 14, but showing the wand at a fourth position and orientation.
Figure 21:
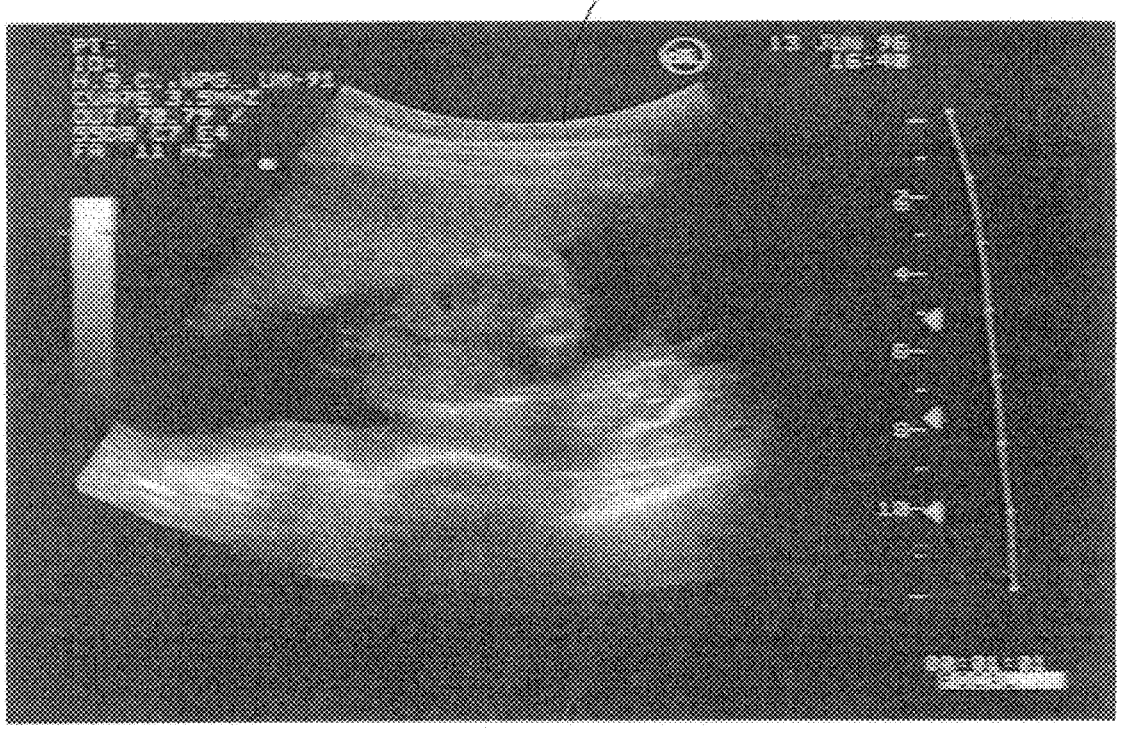
FIG. 21 is a view similar to that of FIG. 15, but showing a CRT display for an ultrasound image slice obtained with the ultrasound wand located as shown in FIG. 20.

In an exactly similar manner, additional sonograms 82-2 through 82-4 are obtained of fetus L, as shown in FIGS. 16–231. Using the transformation method described above, a three-dimensional representation of fetus 80L is then visually constructed in image space 79. Three-dimensional images 80, such as that of fetus 80L may be displayed on a system monitor 83, and electronically stored for future access.

The process used to position the ultrasound image slices in 3D space to thereby enable three-dimensional visualization of an object scanned by an ultrasound beam is described in somewhat greater detail below.

Background

There is understood to be a coordinate system, XYZ, based on the camera's point of view, with the following characteristics:

the viewpoint (or 'eye') is at $(O, O, O)_0$ the camera is looking in the negative-Z direction the positive-X axis extends to the right of the camera's view the positive-Y axis extends to upward in the camera's view There is also a coordinate system, xyz, for each ultrasound frame based on the target rectangle attached to the ultrasound wand, with the following characteristics (assuming that the wand is pointing downward as we look at the target plate with its Y-axis pointing to:

the origin $(O, O, O)_t$ is the lower left corner of the target rectangle the positive-x axis extends to the right along the bottom edge of the rectangle the positive-y axis extends upward along the left edge of the rectangle the positive-z axis extends perpendicular to the target rectangle, toward us Within a target's coordinate system, each image pixel's location can be calculated, knowing the following:

xyz position of the top-center point of the acquired image (given in cm as, for example, (u.0, −3.0, −1.0))

size of a pixel in x and y direction (for example, each equal to 0.025 cm)

The method of the present invention utilizes placement of the pixel data from each frame into a single 3-D space based on the camera's view. This requires transformation from each target's coordinate system to the camera's coordinate system.

A 4×4 transformation matrix may be used to represent any combination of the translation, rotation and scaling of a 3-dimensional coordinate system. Thus, the matrix describes translation of the origin, rotation of xyz axes to another orientation, and optionally, change in scale (although re-scaling is not required in this application). Any number of separate translation and rotation steps can be combined into a single transformation matrix, which will contain the result of all steps performed in sequence.

In the present application, each ultrasound frame provides the following:

grayscale image from ultrasound imaging system target rectangle measurement data from vision system; i.e., position, aim, rotation Procedure The target-to-camera coordinate system transformation matrix is calculated for an ultrasound frame from the position, aim and rotation values for the frame. The image pixel data for this frame is then transformed into the camera's coordinate system by multiplying each pixel's xyz location in the target's coordinate system by this transformation matrix.

Figure 22:
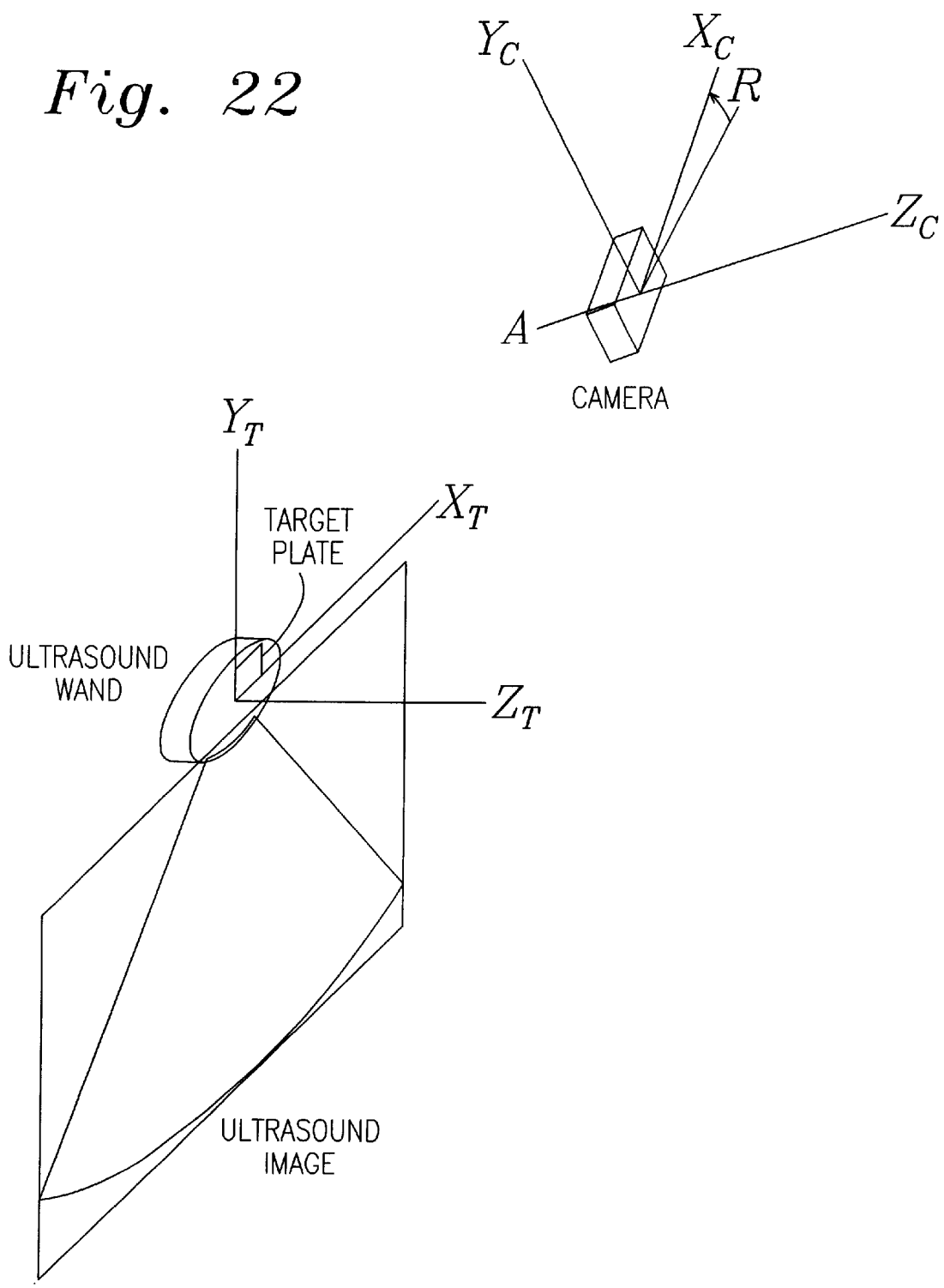
FIG. 22 is a diagrammatic view showing the coordinate system of a target plate/ultrasound wand, and that of a camera used to image the target plate.

Referring now to FIG. 22, the 4×4 target-to-camera transformation matrix can be determined from these given values:

p 3-element floating-point vector $(XYZ)_T$ giving the position of the camera in the target's coordinate system.

a 3-element floating-point vector (xyz) giving the position of a point directly ahead of the camera in the target's coordinate system (this defines the −Z-axis of the camera's coordinate system).

r A floating-point scalar giving the angle between bottom edge of the photograph and the line where the plane of the photograph intersects the plane of the target plate. (In radians.)

To generate the transformation matrix, the camera coordinate system axis vectors $XYZ_C$ are calculated with respect to the target coordinate system with axes $XYZ_T$:

Z-axis

Z has a direction from point a to point p (opposite the aim vector).

X-axis

The direction L is calculated; i.e., the direction of the line of intersection of the xy plane and the XY plane (Z).

XY Plane

L is equal to the cross product of the normal to the xy plane (z) and the normal to XY plane (Z).

Vector L is rotated by R radians on the XY plane:

Rotations qy and x around y are then calculated to bring vector Z to point along z-axis Vector L is rotated by R radians on the xy plane.

Opposite rotations −qy and −qx are applied to bring rotated vector L to point within the XY plane, giving final X vector.

Y-axis

Vectors X and Z and the right-hand rule, give vector Y.

X and Z are combined together, and rotations iz, iy, ix (around z,y,x) needed to bring them to match x and z calculated.

The transform of rotations rz, ry, rx is calculated

Point-P is transformed to calculate the target origin point in camera coordinate system The translation of that point is added to the transform to complete the matrix Having calculated the transformation matrix, each pixel point is multiplied by this matrix to determine its position in camera space.

What is claimed is:

1. A method for forming a three-dimensional view of a plurality of quasi two-dimensional sensor image slices of an object acquired by an imaging sensor, said method comprising;

a. positioning a target device having a target plane containing known contrasting visual features in fixed relationship to an imaging sensor, b. utilizing said imaging sensor to generate a sequence of sensor image scans in known relationship to said sensor to thereby form a plurality of sequential quasi two-dimensional image slices of an object, said image slices bearing a known geometrical relationship to said sensor, c. forming an optical image of said target device for each said sensor imaging scan using an optical imaging system that has an optical axis which may be inclined at an arbitrary oblique angle to a normal to said target plane, d. determining a first coordinate transformation that maps an oblique optical image of said target device into a normal view thereof, e. mapping by said first coordinate transformation each said optical image of said target device into a normal optical image thereof, f. utilizing said first coordinate transformation and said known relationship of said sensor image scan to said sensor to orient and position each quasi two-dimensional image slice into a transformed image slice in a fixed coordinate system containing said object.

2. The method of claim 1 wherein said imaging scan is further defined as comprising an ultrasonic energy beam.

3. The method of claim 2 wherein said sensor is further defined as being an ultrasonic transducer.

4. The method of claim 1 further including the step of determining the size of selected features of said object.

5. The method of claim 4 wherein said size determination step includes measuring the length of features of said normal image of said target device, dividing the measured length by the real world length of the corresponding feature of the actual target device to obtain a ratio k, and multiplying the length of selected object features in said transformed image slice by k.

6. The method of claim 1 wherein said target device is further defined as having thereon at least a first pair of optimally imageable intersecting lines.

7. The method of claim 6 wherein said first pair of intersecting lines is further defined as forming a first corner of a polygon.

8. The method of claim 7 wherein said target device is further defined as having thereon a second pair of optically imageable intersecting lines, said second pair of intersecting lines forming a second corner of said polygon.

9. The method of claim 8 wherein said polygon is further defined as being a quadrilateral.

10. The method of claim 9 wherein said quadrilateral is further defined as being a rectangle.

11. The method of claim 6 wherein said first pair of optically imageable lines on said target device is further defined as having on one side thereof an area of one color and on an opposite side thereof an area of a contrasting color.

12. The method of claim 6 wherein said target device is further defined as having therein a transparent region.

13. The method of claim 6 wherein said target device is further defined as having through the thickness dimension thereof a perforation.

14. A method for forming a three-dimensional view of a plurality of quasi two-dimensional sensor image slices of an object acquired by an imaging sensor, said method comprising;

a. affixing a target plate having a target plane containing known contrasting visual features to an imaging sensor, b. forming a sequence of sensor images of an object using said imaging sensor, each of said images comprising a quasi two-dimensional sensor image slice of said object, each slice bearing a known geometrical relationship to said sensor and said target plate, c. forming an optical image of said target plate for each said sensor image slice, using an optical imaging system that has an optical axis which is in general inclined at an arbitrary oblique angle to a normal to said target plane, d. calculating a first coordinate transformation that maps each oblique optical image of said target device into a normal optical image thereof, e. mapping by said first coordinate transformation each oblique optical image of said target device into a normal optical image thereof, f. utilizing said first coordinate transformation and said known geometrical relationship between each of said sensor image slices and said target plate to calculate a second coordinate transformation which arranges each sensor image slice into correct orientation, size and position relative to each other sensor image slice in a fixed coordinate system containing said object.

g. constructing directrix lines between image contours of adjacent ones of said image slices in said fixed coordinate system to thereby form and display a surface of a three-dimensional representation of said object.

15. The method of claim 14 wherein said imaging sensor is further defined as an ultrasonic transducer.

16. The method of claim 15 wherein said ultrasonic transducer is further defined as having a fan-shaped sensor image field of view, whereby said quasi two-dimensional sensor image slices are fan-shaped.

17. The method of claim 14 wherein said optical imaging system is further defined as including in combination electronic camera means for forming an electronic representation of said optical image, and electronic memory means for storing said electronic images and associating each of said electronic images with one of said sensor image slices.

18. An apparatus for forming a three-dimensional view of a plurality of quasi two-dimensional sensor image slices of an object acquired by an imaging sensor, thereby enabling visualization of said object in a three-dimensional space, said apparatus comprising;

a. a target device having quantifiable visual features adapted to attachment to an imaging sensor, said sensor adapted to acquire a sequence of two-dimensional sensor image slices of an object, b. an optical imaging system for forming a sequence of electronically recordable oblique optical images of said target device attached to said imaging sensor during acquisition of each of said sequence of two-dimensional slices, c. first memory means for storing a sequence of electronically recorded optical images formed by said optical imaging system and associating each said optical image with an electronically recorded sensor image slice acquired simultaneously with said optical image, d. second memory means for storing a sequence of said sensor image slices acquired concurrently with acquisition of said sequence optical images, and for associating each said sensor image slice with a corresponding one of said optical image, e. means for performing a first coordinate transformation that maps each oblique optical image of said target device into a normal optical image thereof, f. means for mapping by said first coordinate transformation each oblique optical image of said target device into a normal optical image thereof, g. means for calculating from said first coordinate transformation a second coordinate transformation which arranges each sensor image slice into correct orientation, size and position relative to each other sensor image slice in a fixed coordinate system containing said object, and h. means for visually constructing directrix lines between image contours of adjacent ones of said image slices in said fixed coordinate system to thereby form and display a surface of a three-dimensional representation of said object.

19. The apparatus of claim 18 further including said imaging sensor.

20. The apparatus of claim 19 wherein said imaging sensor is further defined as being an ultrasound wand.

21. The apparatus of claim 18 wherein said target device is further defined as having thereon at least a first pair of optically imageable lines thereon.

* * * * *